United States Patent [19]  [11]  4,311,709
Dybas et al.  [45] * Jan. 19, 1982

[54] LOWERALKYL SUBSTITUTED DIPHENYL POLYAMINE AS AN ANTIMICROBIAL AGENT

[75] Inventors: Richard A. Dybas, Somerville; Nathaniel Grier, Englewood; Bruce E. Witzel, Rahway, all of N.J.

[73] Assignee: Merck & Co., Inc., Rahway, N.J.

[ * ] Notice: The portion of the term of this patent subsequent to Oct. 23, 1996, has been disclaimed.

[21] Appl. No.: 106,980

[22] Filed: Dec. 26, 1979

[51] Int. Cl.³ ........................................... A61K 31/135
[52] U.S. Cl. ................................................... 424/330
[58] Field of Search ........................................ 424/330

[56] References Cited
U.S. PATENT DOCUMENTS 4,172,094  10/1979  Dybas et al. ...................... 424/330

*Primary Examiner*—Sam Rosen
*Attorney, Agent, or Firm*—David L. Rose; Harry E. Westlake

[57] ABSTRACT

Loweralkyl substituted diphenyl polyamines are useful antimicrobial agents, as well as algae inhibitors. They are especially useful because of their low toxicity. One particular compound, 1-amino-3-{{3-[4-(1-methylethyl)-phenyl]-1-{2-[4-(methylethyl)-phenyl]ethyl}-propyl}amino}-2-propanol, and salts thereof is particularly useful as an udder wash and teat dip for mastitis prevention in lactating cows. Compositions for such use are disclosed.

10 Claims, No Drawings

LOWERALKYL SUBSTITUTED DIPHENYL POLYAMINE AS AN ANTIMICROBIAL AGENT

DISCLOSURE OF THE INVENTION

This invention relates to polyamines which are useful as broad spectrum antimicrobial agents, as well as algae inhibitors. One such compound is especially useful because of a surprisingly low toxicity and as such is particularly suitable for topical use as an udder wash and teat dip for the prevention of mastitis in lactating dairy cows. This novel compound has the structural formula:

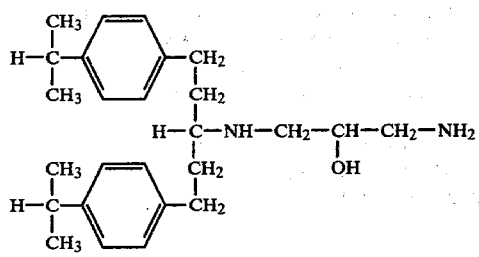

The above compound for the prevention of mastitis in lactating cows is named as 1-amino-3-{{3-[4-(1-methylethyl)phenyl]-1-{2-[4-(methylethyl)phenyl]-ethyl}propyl}amino}-2-propanol. The compound, and its salts are used as an udder wash and teat dip to destroy the population of mastitis associative bacteria on udder skin surfaces.

The compound of this invention is preferably prepared according to the following sequence of reactions:

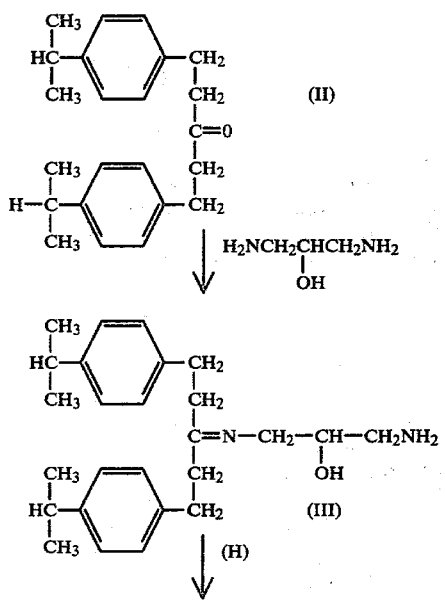

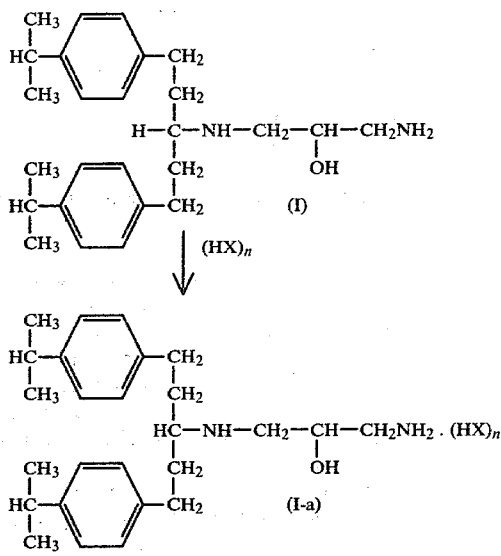

where HX is a mono or polybasic organic or inorganic acid, where sufficient HX is provided to protonate at least one amino group of phenyl polyamine compound I, to form salt I(a). The term n may be 1 or 2 indicating that disalts may be formed with acids with monobasic acids.

The preparation of phenyl polyamine I comprises the Schiff base reaction of the appropriate ketone II and the amine, 1,3-diamino-2-propanol.

To prepare Schiff base III, ketone II and the amine are dissolved in a suitable inert solvent, for example, toluene, and heated to reflux, until reaction is substantially complete. Usually 5 to 20 hours is sufficient for water removal by azeotropic distillation. The solvent is then removed under reduced pressure and the residue comprising the Schiff base III is dissolved in an inert solvent preferably an alkanol, such as ethanol or isopropanol.

In addition, a water miscible solvent may be used which will dissolve the water liberated during the reaction. The same reaction time as with toluene is suitable. Loweralkanols such as ethanol are preferred. The loweralkanol solution may then be used directly in the reduction step.

After dissolution, the Schiff base III is catalytically or chemically reduced.

In catalytic reductions, hydrogen saturates an alkanol solution of Schiff base III using agitation in the presence of the usual hydrogenation catalysts, such as transition metals and their reducible oxides. Especially effective catalysts are the noble metals and their oxides. A particularly preferred catalyst is platinum oxide. Generally, the hydrogenation reaction is carried out in a manner well known in the art. Small particles, e.g., 100–300 mesh of catalyst are admixed with the Schiff base and excess amine in alcohol and placed in a closed system pressurized with from 3–5 atmospheres of hydrogen gas. After reaction is complete, the pressure is released and the catalyst separated from the reaction mixture by filtration. The filtrate containing the phenyl polyamine I, is then further purified by usual techniques. Preferably, whatever solvent may be present is removed under reduced pressure, the residue then dissolved in a water-immiscible solvent, washed with water, followed by a further washing with a saturated aqueous inorganic salt solution. After drying, the solvent is removed by evaporation under reduced pressure giving the phenylpolyamine I usually as an oil. The phenylpolyamine can then be redissolved in loweralkanols, mixtures of loweralkanols and water, diethylether, dioxane and then neutralized with an acid, e.g., hydrogen chloride, or neutralized directly with aqueous acids.

Pharmaceutically acceptable acid addition salts I(a) are then isolated, if desired, by precipitation, evaporation or other usually employed techniques.

Suitable anions X for the salt I(a) include anions derived from inorganic acids as well as those of organic acids such as for example halide, i.e., chloride, bromide or iodide or sulfate, nitrate, bisulfate, phosphate, acetate, propionate, maleate, succinate, laurate, palmitate oleate, stearate, ascorbate, gluconate, citrate, carbonate bicarbonate, benzoate, salicylate, pamoate, phthalate, furoate, picolinate, dodecylbenzenesulfonate, lauryleth-er-sulfate, nicotinate and the like. Generally, any pharmaceutically acceptable anion derived from an acid is suitable and satisfactory when the polyamine salt anion $X^-$, e.g., chloride is replaced with other anions, by well known anion exchange techniques.

Alternatively, a chemical rather than a catalytic reduction is employed to reduce Schiff base III to product I.

In this chemically reductive procedure, the ketone II is reacted with the appropriate amine as before, but the Schiff base VI dissolved in an alkanol or inert ether-type solvent is reacted with a chemical reductant such as sodium borohydride or lithium aluminum hydride, respectively.

Although as little as an equivalent of the chemical reductant can be used successfully, more satisfactory results are obtained if at least two molar excess of and preferably at least a 2.5 molar excess of the chemical reductant is employed. After any initial reaction has subsided, the reaction mixture may be heated at reflux for an hour or two, then cooled to room temperature, and afterwards concentrated under vacuum. The residue obtained is then further purified as by treatment with mineral acid or inorganic base as was described for polyamine I and the salt may thereafter be formed as previously described.

The diphenyl ketones II are readily prepared and two alternative methods, as set forth below.

(A) The Condensation of Acids—This method involves the following reaction scheme:

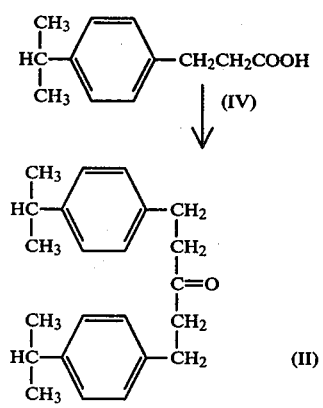

Acylative decarboxylation of carboxylic acid IV is employed by heating the acid at elevated temperatures wither with transition metals, preferably iron, transition metal oxides, alkaline earth oxides, with polyphosphoric acid or with boron trifluoride. Acylative reaction may be achieved by passage of acid vapors over catalysts such as heated thoria aerogel. The preferred reaction comprises admixing carboxylic acid IV with reduced iron powder and stirring in an inert atmosphere at 195° C. to 200° C. for 1–6 hours to form an iron salt.

Preferably, the carboxylic acid IV and iron are agitated under an inert atmosphere of nitrogen for at least 2 hours at 195° C. to 200° C.

After 2 hours, the temperature is increased suitably to 290° C. to 310° C. and agitation continued for at least another three hour period, four hours usually being sufficient. The reaction mixture is allowed to cool, and then is extracted with a suitable inert solvent such as diethylether and filtered. The solvent extracts are concentrated under reduced pressure. The residual liquid is distilled under vacuum to isolate the ketone II.

The carboxylic acids IV employed above are prepared by various means well known in the art.

(B) Condensation of a Grignard and a Nitrile

The diphenyl alkanone may also can be obtained according to the following reaction scheme:

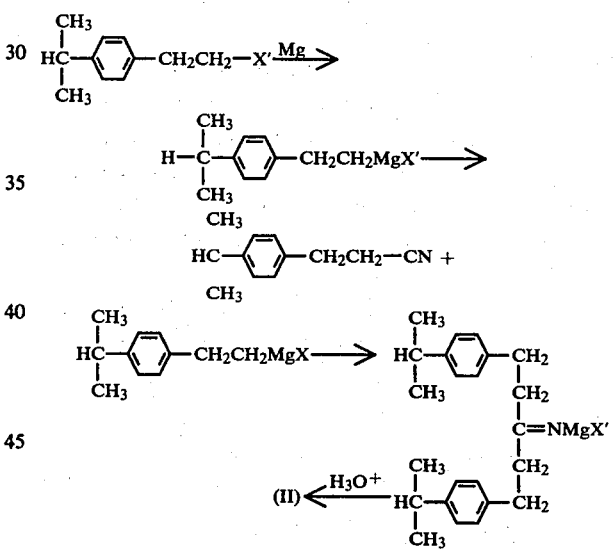

wherein X' is chloro or bromo.

This general procedure utilizes the reaction of a Grignard reagent prepared from a chloro- or bromo-substituted phenyl derivative with a cyanosubstituted phenyl derivative. The resultant disubstituted iminoalkane Grignard complex is hydrolyzed with aqueous mineral acid to the corresponding ketone.

The Grignard reagent is obtained by reaction of the halide with magnesium metal, usually in the form of turnings or powder and may be catalyzed by very small concentrations of iodine or methyl iodide. Solvents which are useful include diethyl ether, dibutyl ether, tetrahydrofuran, dioxane and benzene. Usually, gentle warming suffices to initiate the reaction and the halide is gradually added to the metal-solvent mixture. After complete addition, the disappearance of practically all magnesium metal signifies the end of the reaction. A small excess of halide is used and moisture must be excluded; a nitrogen atmosphere is beneficial. The Grignard reagent is then added to the nitrile, which is previously dissolved in two or three times its volume of solvent, over a period of 15 minutes to 1 hour at ambient temperature.

The reaction mixture may then be heated to reflux to insure complete reaction. Generally, a small excess of Grignard reagent as compared to nitrile is employed. From 1 to 10 hours at reflux is sufficient for complete conversion. The resultant imine salt is preferably decomposed and hydrolyzed to the ketone with aqueous mineral acids such as hydrochloric, sulfuric and phosphoric. The ketones are water-insoluble and may be extracted with water-immiscible solvents. Purification is preferably accomplished by fractional distillation under reduced pressure. It is feasible to use the crude ketone reaction mixture for the alkylation of diamines as the Grignard reaction by-products are usually alcohols or hydrocarbons and do not react with amines. The reactant halides, if present in the crude product, should be removed prior to the ketone-amine alkylation process.

The concentrations of Grignard reagent and nitrile may be varied over wide limits for securing good yields in the process. The halide and cyano, as well as carboxylic derivatives of phenyl compounds, e.g., phenylpropanoic acid are readily available.

Once the ketone II is obtained it can then be reacted with a suitable diamine. The ketone and amine which react under the above conditions to form the desired mastitis preventive compound are di[2-(4-isopropylphenyl)ethyl]ketone and 1,3-diamino-2-propanol respectively.

The present invention relates to a method and compositions for eradicating or drastically reducing the number of mastitis producing organisms commonly found on skin surfaces of economically important domestic animals, especially dairy cows and particularly in the region of the udder and teats.

The effective microbial inhibitor encompassed by the present invention is 1-amino-3-{{3-[4-(1-methylethyl)phenyl]-1-{2-[4-(1-methylethyl)phenyl]-ethyl}propyl}-amino}-2-propanol, its acid salts and preferably the dihydrochloride salt monohydrate. Gram positive, gram negative bacteria, certain yeasts and various fungi are destroyed or rendered static by concentrations ranging from less than one to one-thousand parts per million, and many are controlled with concentrations of from one to one-hundred parts per million.

The present compositions consist essentially of a preparation which when rendered for use contains from about 0.1 to 5 percent by weight of active ingredient based on the total weight of the composition, preferably from 0.1 to 2%. The active ingredient consists of 1-amino-3-{{3-[4-(1-methylethyl)phenyl]-1-(2-[4-(1-methylethyl)phenyl]-ethyl}propyl}amino}-2-propanol, its acid salts and hydrates thereof.

The active ingredient is preferably formulated with relatively non-volatile film-forming agents, and these film-forming agents may be present in the final compositions at from 0.1 to 5% by weight based on the total weight of the composition. Generally 0.5% to 1% is sufficient to provide a residual action. The requirement for an emollient to counteract potential skin damage such as irritations and cracking due to these formulations is unnecessary. The remainder consists essentially of inert ingredients and may range from 90 to 99% of total composition and includes primarily water, surface active agent, surfactants preferably non-ionic or cationic types, odorants, colorants and the like. Emollients may be added to alleviate pre-existing skin damage such as from prior treatments e.g. sodium hypochlorite or weathering factors. Carriers into which the active ingredients of this invention may be incorporated include lotions, ointments, water solutions, aerosols, creams, pulverized mixtures, gel sticks and the like. Among the various additives which may be employed are polyoxyethylene sorbitan trioleate, polyethyleneglycols up to 6000 molecular weight, surfactants and emulsifiers e.g. nonylphenolpolyethoxylate, glyceryl monostearate, diethylaminoethylalkylamide phosphate, isopropyl myristate, octyl alcohol, glyceryl and glycol esters of stearic acids, glycols such as propylene glycol, glycerine, sorbitol, alcohols such as ethanol, isopropanol, propellants such as halogenated hydrocarbons e.g. dichlorodifluoromethane, trichlorofluoromethane, carbon dioxide, nitrogen, solid diluents such as starch, talc, and perfumes.

Worldwide, the dairy industry uses a recommended regimen to minimize the incidence of mastitis comprised of a pre-milking sanitizer udder wash and a postmilking teat dip with the same preparation. Most of the products employed contain as active ingredients available halogen such as a 5% hypochlorite solution 0.5 to 2% of chlorinated triazinones or hydantoins, iodophores containing 0.05 to 1% iodine, 0.1 to 0.5% of quaternary ammonium salts, chlorhexidine at usually 0.2 to as high as 1.0% solution and others. Each type has significant deficiencies, with teat and skin cracking and drying almost universal so that emollients such as glycerine, oils, ointments and other agents must be incorporated to offset irritation and skin damage. Some formulations such as the quaternary ammonium type, and chlorhexidine are poorly effective against gram negative pathogens such as *Pseudomonas* species, and reports indicate these bacteria can selectively involve such treated areas. Other difficulties encountered with some also include penetration and absorption into skin so that the milk becomes contaminated; eye or skin irritations and sensitization to the handlers especially when spray application is made; partial loss of effectiveness when mixed with hard water or in the presence of low milk concentrations, and accelerated corrosion and deterioration of milking machine equipment.

The products of this inventions have a broad inhibitory spectrum and high potency. One test system employed seven different mastitis pathogens inoculated onto separate Mueller-Hinton agar plates which contained 1, 5, 10, 20, 40, 80 or 100 mcg./ml. of the cited dihydrochloride final concentration. After incubation for 18-24 hours at 37° C., the minimal inhibitory concentration was determined as that showing less than one colony per plate; all assays were made in duplicate. The MIC's in mcg./ml. observed were: *Streptococcus dysgalactiae*, 1; *Streptococcus uberis*, 1; *Streptococcus agalactiae*, 1; *S. aureus*, 5; *E. coli*, 5; *Klebsiella* sp., 5; and *Pseudomonas aeruginosa*, 80. In a different antimicrobial assay similar effectiveness was measured for *B. subtilis*, *Streptococcus pyogenes*, *Bordetella bronchiseptica*, *Salmonella schottmuelleri*, *Pasturella multocida*, *Corynebacterium pseudodiphtherium*, *Fusarium* sp., *Cephalosporium* sp., *Tricophyton mentagrophytes*, *Aureobasidium pullulans*, and *Candida* sp.

Additional efficacy studies were made using a laboratory modification of the National Mastitis Council's Protocol A with excised cow's udder in vitro. Prepared teats were dipped to a depth of approximately 15 mm. into a skim milk inoculum containing the test bacteria and then allowed to drain for 5 minutes. Then each teat was dipped into a distilled water solution of the cited dihydrochloride salt using concentrations which ranged from 0.05 up to 1% to a depth of 25 mm. After a period of 10 minutes the removal of any surviving organisms was accomplished by rinsing the teats using 5 ml. of a quenching solution of lecithin (0.05%), tween-80 (0.5%) and sodium thiosulfate (0.5%). The rinse solutions were diluted in sterile saline, plated on an appropriate medium and incubated at 37° C. for 18–20 hours. Colonies were then counted for only those plates with 15–300 colonies, and all dilutions were plated in duplicate. The percent reduction in microorganisms on the teat surfaces was determined using as controls the inoculated teats dipped in sterile distilled water. A 0.5% solution of the 1,3-diamino-2-propanol dihydrochloride derivative provided greater than 99.8% kill against *Pseudomonas aeruginosa, Streptococcus uberis, Streptococcus agalactiae, E. coli, Klebsiella* sp. and from 98 to 99.8% for *S. aureus* and *Streptococcus dysgalactiae*. A 0.1% solution caused a 99% reduction for *Pseudomonas aeruginosa*. These potencies may be significantly enhanced, if desired, by use of adjuvants.

Surprisingly, in light of the high antimicrobial activities noted, the cited compound is of low toxicity and practically non-irritating on skin. The acute oral LD50 (mice) is 1300 mg./kg. of body weight administered at a concentration of 100 mg./ml. in 1% aqueous methylcellulose (100 cps). A 1% solution in distilled water applied to either intact or abraded dorsal skin of shaved areas (rabbits) and maintained at the test sites under an occlusive dressing for 24 hours, and observed for two weeks, proved essentially non-irritating; at a concentration of 5% in distilled water the compound was slightly irritating with no signs remaining after seven days. A 0.1% concentration was very slightly irritating to the eye with effects disappearing within 24 hours. Thus instead of contributing to or initiating skin cracking and drying the diaminopropanol derivative should promote healing of damaged skin areas whether inflicted mechanically, by weather conditions or as the result of exposure to toxic chemical treatments.

Preliminary experiments indicate that upon application of a 1% solution to the udder under conditions paralleling that to be used commercially no detectable residues could be established in the milk. The sensitivity of the analytical method employed met the stringent criteria set by various governmental agencies. Evidently, the compound appears unable to penetrate the skin and may be tightly bound to the surface.

The compounds of this invention may be employed in various forms as antiseptics for skin. The preferred acid addition salts are generally solids and may be water soluble or water insoluble. These include the hydrochloride, nitrate, phosphate, sulfate, acetate, citrate, gluconate, propionate, butyrate, maleate, fumarate, lactate, malate, succinate, laurate, tartrate, stearate, benzoate, sulfosalicylate, pamoate and the like. The water-soluble salts may be packaged in pre-measured bags which can be opened and dissolved into a given amount of water, or in pre-measured water-soluble bags which can be thrown into the prescribed amount of water until bag and contents are dissolved. Both polyethyleneoxide and polyvinyl alcohol-derived bags are suitable. The water-insoluble acid addition salts should be admixed with sufficient surfactant, preferably of the non-ionic or cationic types so that upon addition to water good wetting and dispersion are obtained. Preparations and formulations herein described which require no emollients represent a significant economic advantage in that there is no shipment of water or other vehicle, and containers may be smaller and less costly than those for solutions, emulsions and dispersions.

The compounds of this invention, when used in such compositions are generally supplied as a concentrate or premix which may be liquid or solid. The active ingredient is present in greater amounts for dilution to the concentration of actual use. In such concentrates or premixes, the active ingredient may be present in from about 10 to 100% by weight.

Further, the use of relatively non-volatile film forming agents as carriers rather than emollients serves to enhance potency by increasing residual inhibitory action on skin and does not decrease efficacy as experienced with certain of the presently used commercial dip products. Also much lower levels suffice, as for example with glycerine and the like. No emolliency is acquired with concentrations of glycerine below 5% and usually 10% is required, whereas for film-forming and enhanced antimicrobial action with the compounds of this invention a maximum concentration of 2% glycerine should suffice. Other adjuvants which may be employed similarly include propyleneglycol, polyethyleneglycol, methylcellulose, hydroxyethylcellulose, water-soluble gums, sodium alginate, polyvinylpyrrolidone, emulsified oils and others. These film-forming agents and the antimicrobial can be removed by washing before milking.

A variety of food grade colorants may be added to the compositions or compounds so that animals which have been treated can be readily distinguished and the extent of surface coverage easily observed. There are commercially available a spectrum of dyes such as FD&C Blue No. 1, red No. 3 lake, green No. 3, yellow No. 6 lake, and blue No. 1, carbon black dispersions and the like. About 0.0001–5% of food grade water-dispersible or water soluble colorant in the composition should meet most requirements.

Additional formulation components may include odorants, other sequestrants such as triethanolamine tris-(hydroxymethyl)aminomethane, or glycine and for lowering viscosity, alcohols such as ethyl or isopropyl.

The teat dips are used generally after milking and they may be in the form of solutions, emulsions, creams and ointments. Application may utilize immersions of teats into liquids, spraying liquids directly upon the relevant skin surfaces which harbor potential infectious microorganisms or as with the more viscous compositions manually spreading over the areas. An udder wash usually precedes milking; the liquid compositions may be applied to the surface as with a sponge or soft brush, allowed to remain for periods up to ten minutes and then are removed by water rinses. Creams and ointments of a water soluble or dispersible base formulation may be employed similarly, but the increased labor required makes the liquid wash a preferred procedure.

The free base and salts are generally noncorrosive and may be used in contact with iron, stainless steel, rubber, plastic and glass, especially when diluted or dispersed with water.

EXAMPLE 1

1-Amino-3-{{3-[4-(1-methylethyl)phenyl]-1-{2-[4-(1-methylethyl)phenyl]ethyl}propyl}amino]-2-propanol To a solution of 1,3-diamino-2-propanol (20 g., 0.22 m.) in ethanol (200 ml.) at 90° C. (bath temperature) is added dropwise, with stirring, a mixture of di[2-(4-isopropylphenyl)-ethyl]ketone (6.5 g., 0.02 m.) and ethanol (20 ml.) over ca. 40 minutes. The mixture is kept overnight (ca. 15 hours) under gentle reflux (bath at 95°–100° C.), allowed to cool, and transferred to a Parr hydrogenation apparatus. Platinum oxide (2.0 g.) is added, and the mixture reduced at room temperature under a 40 p.s.i. hydrogen atmosphere until hydrogen uptake ceases.

The reaction mixture is then filtered from the catalyst, the ethanol removed in vacuo, the resultant oil distributed between ether (ca. 200 ml.) and an equal volume of water, and the separated ether layer washed with additional (3×200 ml.) water. The dried (anhydrous sodium sulfate) ether solution is filtered and the ether removed in vacuo to leave 1-amino-3-{{3-[4-(1-methylethyl)phenyl]-1-{2-[4-(1-methylethyl)phenyl]ethyl}propyl}amino]-2-propanol in essentially quantitative yield as a clear, nearly colorless oil.

EXAMPLE 2

Dihydrochloride and Dipropionate Salts of 1-Amino-3-{{3-[4-(1-methylethyl)phenyl]-1-{2-[4-(1-methylethyl)phenyl]ethyl}propyl}amino]-2-propanol To a cooled (ice-bath cooling) solution of 1-amino-3-{{3-[4-(1-methylethyl)phenyl]-1-{2-[4-(1-methylethyl)phenyl]ethyl}propyl}amino]-2-propanol in isopropanol (about 5 ml. of isopropanol for each gram of free base) is added anhydrous hydrogen chloride gas with stirring. When precipitation is complete, the resultant dihydrochloride is filtered. Recrystallization from isopropanol (95), water (5), (about 5 ml. of solvent for each gram of product) yields 1-amino-3-{{3-[4-(1-methylethyl)phenyl]-1-{2-[4-(1-methylethyl)phenyl]ethyl}propyl}amino]-2-propanol dihydrochloride monohydrate, m.p. 263°–265° C.

The dihydrochloride is also prepared by treatment of the free base in ether with gaseous hydrogen chloride or with isopropanol saturated with hydrogen chloride.

To a stirred solution of 1-amino-3-{{3-[4-(1-methylethyl)phenyl]-1-{2-[4-(1-methylethyl)phenyl]ethyl}propyl}amino]-2-propanol (3.97 g., 0.01 m.) in anhydrous ether (ca. 50 ml.) is added dropwise over ca. 10 minutes a mixture of propionic acid (1.49 g., 0.02 m.) and ether (10 ml.). The resultant mixture is allowed to stir at ambient temperature for several hours, and the ether then removed in vacuo to yield 1-amino-3-{{3-[4-(1-methylethyl)-phenyl]-1-{2-[4-(1-methylethyl)phenyl]ethyl}propyl}amino]-2-propanol dipropionate.

EXAMPLE 3

Water-soluble powder

| Ingredients: | Amount |
|---|---|
| 1-Amino-3-{{3-[4-(1-methylethyl)phenyl]-1-{2-[4-(1-methylethyl)phenyl]ethyl}propyl}amino]-2-propanol dihydrochloride monohydrate | 10 gm. |

The free-flowing powder is packed in moisture-proof paper envelopes preferably having an aluminum barrier or in water-soluble polyvinyl bags protected from moisture. The contents 10 gm., are added to 1 liter of ordinary tap water to provide an approximately 1% wt/volume solution suitable for use as a teat dip or udder wash.

EXAMPLE 4

Water-soluble powder

| Ingredients: | Amount |
|---|---|
| 1-Amino-3-{{3-[4-(1-methylethyl)phenyl]-1-{2-[4-(1-methylethyl)phenyl]ethyl}propyl}amino]-2-propanol digluconate | 5 gm. |
| Fumed silicon dioxide | 0.1 gm. |

The powders are thoroughly mixed, packaged as in Example 3 and used identically to provide a 0.5% wt/vol. solution. Lower or higher strength solutions are prepared by proportional adjustment of the amount of water.

EXAMPLE 5

Water-dispersible powder

| Ingredients: | Amount |
|---|---|
| 1-Amino-3-{{3-[4-(1-methylethyl)phenyl]-1-{2-[4-(1-methylethyl)phenyl]ethyl}propyl}amino]-2-propanol dilaurate | 14.5 gm. |
| Polyoxyethylenesorbitan tristearate | 1 gm. |
| FD & C Yellow No. 5 | .01 gm. |

The ingredients were dry blended to provide a uniform mixture and packaged in a single envelope. Addition to 500 to 2000 ml. of ordinary tap water with good stirring provided a dispersion ready for use as a teat dip.

EXAMPLE 6

Aqueous solution

| Ingredients: | Amount |
|---|---|
| 1-Amino-3-{{3-[4-(1-methylethyl)phenyl]-1-{2-[4-(1-methylethyl)phenyl]ethyl}propyl}amino]-2-propanol dihydrochloride monohydrate | 10 gm. |
| Glycerine | 5–20 gm. |
| Ethyl alcohol | 5–10 gm. |
| FD & C Blue No. 1 colorant | 1 gm. |
| Water | Sufficient to make 1000gm. of solution |

The formulation is prepared by first dissolving the colorant in a mixture of the ethyl alcohol with approximately 100 gm. of water. Separately, the amine dihydrochloride monohydrate is dissolved in a solution comprising the glycerine and approximately 500 gm. of water. The prepared solutions are admixed with gentle stirring and adjusted to a total weight of 1000 gm. by the addition of water. The formulation which may contain a maximum of 2% by weight of glycerine may be used as such for teat dip and udder wash, or may be further diluted with water. It is also suitable for spray application.

EXAMPLE 7

Solution concentrate

| Ingredients: | Amount |
| --- | --- |
| 1-Amino-3-{{3-[4-(1-methylethyl) phenyl]-1-{2-[4-(1-methylethyl) phenyl]ethyl}propyl}amino]-2- propanol dihydrochloride monohydrate | 100 gm. |
| Glycerine | 100 gm. |
| Water | 800 gm. |

The concentrate prepared by adding the first two components to the water, may be diluted with additional water to make up to 10 liters of solution suitable for a teat dip or udder wash.

EXAMPLE 8

Film-forming aqueous solution

| Ingredients: | Amount |
| --- | --- |
| 1-Amino-3-{{3-[4-(1-methylethyl) phenyl]-1-{2-[4-(1-methylethyl) phenyl]ethyl}propyl}amino]-2- propanol dipropionate | 11.5 gm. |
| Methylcellulose, USP grade | 10 gm. |
| Glycerine | 1.5 gm. |
| FDIC Green No. 3 | 1 gm. |
| Water | 976 gm. |

The methylcellulose is first wetted by mixing thoroughly with 200 gm. of water. To avoid lumping the powder should be slowly added with good agitation. After "wetting out" an additional 300 gm. of water or preferably cracked ice is added and the mixture stirred until a clear solution results. The colorant and glycerine may then be added, followed by an additional 300 gm. of water and then the amine dipropionate salt. After complete solution, the balance of water is added to provide 1000 gm. of formulation. Upon application by teat dip or spray postmilking a pliable film remains, after air-drying, which contains the antimicrobial as an available inhibitor. After about 6 minutes, and just prior to milking, the film is removed with a cool water wash.

EXAMPLE 9

Aqueous emulsion

| Ingredients: | Amount |
| --- | --- |
| 1-Amino-3-{{3-[4-(1-methylethyl) phenyl]-1-{2-[4-(1-methylethyl) phenyl]ethyl}propyl}amino]-2- propanol dilaurate | 14.5 gm. |
| Glycerylmonostearate | 20 gm. |
| Mineral oil, 70 vis | 40 gm. |
| Propyleneglycol | 40 gm. |
| Nonylphenylpolyethyleneglycol ether | 20 gm. |
| Water | 865.5 gm. |

Dissolve the glycolether dispersant and propyleneglycol in the water. Thoroughly mix the first three components of the above formulations, and add gradually to the aqueous solution. A high speed disperser machine is required or a homogenizer. The oil-in-water emulsion is ready for use or can be further diluted with water. It may be used as a teat dip postmilking.

EXAMPLE 10

Water-dispersible ointment

| Ingredients: | Amount |
| --- | --- |
| Hydrophilic ointment USP | 995 gm. |
| 1-Amino-3-{{3-[4-(1-methylethyl) phenyl]-1-{2-[4-(1-methylethyl) phenyl]ethyl}propyl}amino]-2- propanol dihydrochloride monohydrate | 5 gm. |

Application is made postmilking by manual spreading over the teat and udder surfaces. Prior to milking a water rinse suffices to remove the residual formulation.

We claim:

1. A method for the prevention of mastitis in lactating dairy cows which comprises applying to either the udder, teats or both of such lactating dairy cows, a mastitis preventing effective amount of 1-amino-3-{{3-[4-(1-methylethyl)phenyl]-1-{2-[4-(1-methylethyl)-phenyl]ethyl}propyl}amino]-2-propanol and pharmaceutically acceptable salts thereof.

2. The method of claim 1 wherein the mastitis preventing compound is applied to the lactating dairy cows just prior to milking.

3. The method of claim 1 wherein the mastitis preventing compound is applied to the lactating dairy cows just after milking.

4. The method of claim 1 wherein the mastitis preventing compound is applied to the lactating dairy cows just prior to and just after milking.

5. The method of claim 1 wherein the mastitis preventing compounds are sprayed onto the udder and teats of the lactating dairy cow.

6. The method of claim 1 wherein the mastitis preventing compound is applied as a dip to the teats of the lactating dairy cow.

7. A composition useful for the prevention of mastitis in lactating dairy cows which comprises an inert carrier and a mastitis preventing effective amount of 1-amino-3-{{3-[4-(1-methylethyl)phenyl]-1-{2-[4-(1-methylethyl)-phenyl]ethyl}propyl}amino]-2-propanol and pharmaceutically acceptable salts thereof.

8. The composition of claim 7 which contains from 0.1 to 5% by weight of the mastitis preventing compound.

9. The composition of claim 8 which contains from 0.1 to 2% by weight of the mastitis preventing compound.

10. The composition of claim 7 which is a concentrate or premix to be diluted prior to use containing from 10 to 100% by weight of the mastitis preventing compound.

* * * * *